United States Patent
Butler et al.

(10) Patent No.: US 6,703,370 B1
(45) Date of Patent: *Mar. 9, 2004

(54) USE OF RIBOSE TO TREAT FIBROMYALGIA

(75) Inventors: Terri L. Butler, Minneapolis, MN (US); Dean J. MacCarter, Englewood, CO (US); Daryl K. MacCarter, Eagle, ID (US)

(73) Assignee: Bioenergy, Inc., Ham Lake, MN (US)

( * ) Notice: Subject to any disclaimer, the term of this patent is extended or adjusted under 35 U.S.C. 154(b) by 51 days.

This patent is subject to a terminal disclaimer.

(21) Appl. No.: 09/697,034

(22) Filed: Oct. 26, 2000

Related U.S. Application Data

(60) Provisional application No. 60/161,841, filed on Oct. 27, 1999.

(51) Int. Cl.[7] .......... A01N 43/04; A61K 31/70; C07H 1/00
(52) U.S. Cl. ............................ 514/23; 536/1.11
(58) Field of Search .............. 514/23; 536/1.11

(56) References Cited

U.S. PATENT DOCUMENTS

| | | | |
|---|---|---|---|
| 4,605,644 A | 8/1986 | Foker | 514/45 |
| 4,719,201 A | 1/1988 | Foker | 514/23 |
| 4,824,660 A | 4/1989 | Angello et al. | 424/1.1 |
| 4,871,718 A | 10/1989 | Carniglia | 514/23 |
| 4,877,798 A * | 10/1989 | Sorensen et al. | |
| 4,920,098 A | 4/1990 | Cotter et al. | 514/2 |
| 4,968,719 A | 11/1990 | Brevetti | 514/556 |
| 5,114,723 A | 5/1992 | Stray-Gundersen | 426/74 |
| 5,292,538 A | 3/1994 | Paul et al. | 426/74 |
| 5,391,550 A | 2/1995 | Carniglia et al. | 514/23 |
| 5,477,857 A | 12/1995 | McAfee et al. | 128/654 |
| 5,707,971 A | 1/1998 | Fahy | 514/43 |
| 5,714,515 A | 2/1998 | Bunger | 514/557 |
| 5,853,753 A | 12/1998 | Maierhofer et al. | 424/450 |
| 5,895,787 A | 4/1999 | Arffmann et al. | 514/415 |
| 5,922,703 A | 7/1999 | Yu et al. | 514/182 |
| 6,139,819 A | 10/2000 | Unger et al. | 424/9.52 |
| 6,159,942 A * | 12/2000 | St. Cyr et al. | |
| 6,159,943 A * | 12/2000 | Butler et al. | |

FOREIGN PATENT DOCUMENTS

| | | | |
|---|---|---|---|
| EP | 0312249 | 4/1989 | A61K/33/08 |
| EP | 0573466 | 12/1993 | A61K/31/70 |
| EP | 0652012 | 5/1995 | A61K/31/70 |
| EP | 0680945 | 11/1995 | C07C/229/22 |
| EP | 0894439 | 2/1999 | A23L/2/38 |
| WO | WO92/15311 * | 9/1992 | |
| WO | 92/15311 | 9/1992 | A61K/31/70 |
| WO | 94/02127 | 2/1994 | A61K/31/195 |
| WO | 96/18313 | 6/1996 | A23L/1/305 |
| WO | 99/65476 | 12/1999 | A61K/31/00 |

OTHER PUBLICATIONS

Batista, R., et al., "Partial left ventriculectomy—the Batista procedure", *European Journal of Cardio–Thoracic Surgery*, 15 (Suppl, 1), pp. S12–S19, (Jan. 1999).

Bax, J.J., et al., "Accuracy of Currently Available Techniques for Prediction of Functional Recovery After Revasularization in Patients With Left Ventricular Dysfunction Due to Chronic Coronary Artery Disease: Comparison of Pooled Data", *Journal of the American College of Cardiology*, 30 (6), pp. 1451–1460, (Nov. 15, 1997).

Furnary, A.P., et al., "Multicenter Trial of Dynamic Cardiomyoplasty for Chronic Heart Failure", *Journal of the American College of Cardiology*, 28 (5), pp. 1175–1180, (Nov. 1, 1996).

Gross, M., et al., "Metabolism of D–Ribose Administered Continuously to Healthy Persons and to Patients with Myoadenylate Deaminase Deficiency", *Klinische Wochenschrift*, 67, pp. 1205–1213, (1989).

Hegewald, M.G., et al., "Ribose Infusion Accelerates Thallium Redistribution With Early Imaging Compared With Late 24–Hour Imaging Without Ribose", *JACC*, 18 (7), pp. 1671–1681, (Dec. 1991).

Jessup, M., "Optimizing Medical Management of the Patient with Severe Heart Failure Awaiting Cardiac Transplanting", *Cardiology—In Review*, 4 (5), pp. 286–291, (Sep. 1996).

Ma, L., et al., "Nitroglycerin enhances the ability of dobutamine stress echocardiography to detect hibernating myocardium", *Circulation*, Vol, 96, No. 11, pp. 3992–4001, (Dec. 2, 1997).

Mahoney, Jr., J.R., et al., "A comparison of different carbohydrates as substrates for the isolated working heart", *Journal of Surgical Research*, 47, pp. 530–534, (1989).

Nagueh, S.F., et al., "Identification of Hibernating Myocardium: comparative accuracy of myocardial contrast echocardiography, rest–redistribution thallium–201 tomography and dobutamine echocardiography", *JACC vol. 29*, No. 5, pp. 985–993, (Apr. 1997).

Sawada, S.G., et al., "Echocardiographic Detection of Coronary Artery Disease During Dobutamine Infusion", *Circulation*, 83 (5), pp. 1605–1614, (May 1991).

(List continued on next page.)

Primary Examiner—James O. Wilson
Assistant Examiner—Traviss C. McIntosh, III
(74) Attorney, Agent, or Firm—Kathleen R. Terry

(57) ABSTRACT

The present invention relates to methods and compositions comprising ribose for the treatment of fibromyalgia syndrome. The methods and compositions of the invention are especially suitable for oral administration and are useful for alleviating the symptoms of pain, fatigue, and irritable bowel syndrome in fibromyalgia syndrome.

5 Claims, 1 Drawing Sheet

OTHER PUBLICATIONS

Tan, Z.T., et al., "Verapamil, ribose andadenine enhance resynthesis of postischemic myocardial ATP", *Life Sciences*, 55 (*18*), pp. PL 345–PL 349, (1994).

Tullson, P.C., et al., "Adenine Nucleotide Syntheses in Exercising and Endurance–trained Skeletal Muscle", *The American Journal of Physiology*, 261 (*2*), pp. C342–C347, (1991).

Tullson, P.C., et al., "IMP Metabolism in Human Skeletal Muscle After Exhaustive Exercise", *The American Journal of Physiology*, pp. 146–152, (1995).

Wagner, D.R., et al., "Effects of oral ribose on muscle metabolism during bicycle ergometer in AMPD–deficient patients", *Annals of Nutrition and Metabolism*, 35 (*5*), pp. 297–302, (1991).

* cited by examiner

USE OF RIBOSE TO TREAT FIBROMYALGIA

CROSS REFERENCE TO RELATED APPLICATION

This application claims benefit of U.S. Provisional Application Ser. No. 60/161,841, filed on Oct. 27, 1999.

BACKGROUND OF THE INVENTION

Fibromyalgia syndrome is a common yet mysterious condition with symptoms of widespread pain and fatigue. The syndrome afflicts five to ten million Americans, women 20 times more often than men. It occurs worldwide with no particular ethnic correlation. It has been proposed by various researchers that the syndrome is caused by such diverse causes as: growth hormone deficiency, relaxin hormone deficiency, autoimmune (rheumatoid) disorder, spinal cord compression, viral infection (heptatisC virus), injection with rubella vaccine, idiopathic nociceptive dysfunction, silicone implants, and other causes. It has even been suggested that fibromyalgia is a psychosomatic symptom of depression.

Nonetheless, the specificity of symptoms indicates a true syndrome, although primary cause versus side-effects remains unknown. In 1994, it became officially recognized as a diagnosis by the Copenhagen Declaration. The two criteria for the diagnosis of fibromyalgia as defined by the American College of Rheumatology (ACR) are: 1) diffuse widespread pain, and 2) the presence of multiple tender points. The latter comprise 18 points that are extremely painful on palpation. These specific sites are at the base of the occiput, the cervical anterior, the trapezius, the supraspinatus, the second rib, the epicondyle on the elbow region, the greater trochanter, the gluteus, and the fat pad on the knee. It should be noted that many of these tender points are not muscle tissue. In fact, some researchers believe that skin, tendons or the subcutaneous fascia are the primary nociceptive dysfunctional tissues. Accordingly, the syndrome is sometimes referred to as Myofascial Pain Syndrome. Although many patients report joint pain, unless those patients also have rheumatoid or osteoarthritis, the pain in the joints is referred pain from nearby skin, tendons or muscles. Typically, joints are not swollen as in arthritis.

In addition to pain and tender points, patients may experience a disturbed sleep cycle, tension headaches, irritable bowel syndrome, premenstrual tension syndrome, cold intolerance, deconditioning, reduced exercise tolerance and restless leg syndrome. Diagnosis is based on reporting pain in at least 11 of the 18 tender points. Pressure over one of these areas can cause referred pain in peripheral locations.

The symptoms of pain and fatigue are chronic and the intensity varies unpredictably. Patients may find that they are so severely affected that they are unable to work in their professions or perform daily tasks. There is no known cure for fibromyalgia. Among the suggested therapies are: steroids, analgesics, hormone administration, antidepressants, physical therapy, xylocaine injections into the tender points to allow for exercise and education on coping with chronic pain. Most patients can expect to have the symptoms lifelong. The common analgesics seem to have minimal effect. While strong analgesics such as codeine can diminish pain, these cannot be taken for long periods of time. Patients who are able to exercise routinely can experience improvement. Xylocaine injections may give enough temporary relief so that the patients can exercise, but these injections are inconvenient for daily use. For some patients, antidepressants also seem to help. Most doctors treating fibromyalgia patients suggest a combination of medical treatment, moist heat, and exercise. Because of the varied responses to treatment, patients are encouraged to make careful observation of any treatments that seem to offer some alleviation of symptoms and, based on their observations, to devise a personalized regimen. Otherwise, those who are afflicted must learn to live with the symptoms and a greatly reduced quality of life.

The need remains for compositions and methods of alleviating the symptoms of fibromyalgia, without inducing deleterious side effects.

SUMMARY OF THE INVENTION

The present invention relates to methods and compositions for the treatment of fibromyalgia. The present invention provides ribose, alone or in combination with minerals, vitamins, malic acid or ornithine to alleviate pain and fatigue as well as irritable bowel syndrome due to fibromyalgia.

DETAILED DESCRIPTION OF THE INVENTION

Figure 1:
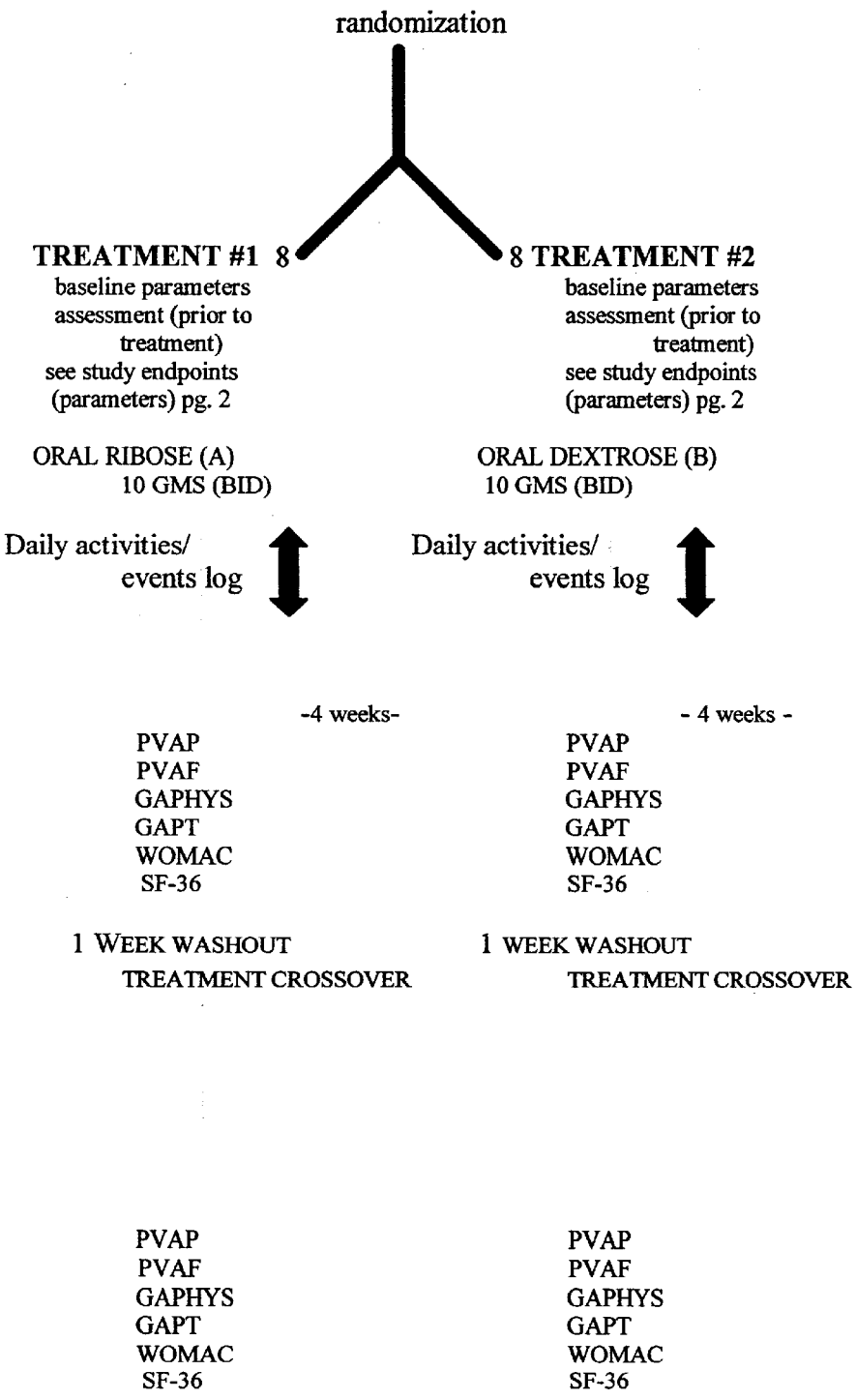
FIG. 1 summarizes the clinical protocol to be followed.

While it is not known whether the pain and fatigue in fibromyalgia are due to neuronal, endocrine, physiological, or genetic factors, an approach that would alleviate some or all of the symptoms of the condition would be an improvement in the current treatment regime. Applicants have disclosed in U.S. patent application Ser. No. 09/290,789, now U.S. Pat. No. 6,159,942, that ribose is useful in raising the energy levels of healthy individuals during intense exercise. In addition, Applicants have also disclosed in pending U.S. patent application Ser. No. 09/405,462, now U.S. Pat. No. 6,339,716, that ribose can prevent and alleviate muscle soreness and cramping in healthy exercising humans and patients with emphysema. However, it is believed that these effects are due to the energy-stimulating effects of ribose administration to subjects with a higher than usual energy demand or lower than usual oxygen availability. We have now unexpectedly found that ribose also alleviates symptoms of pain and fatigue as well as painful irritable bowel syndrome in fibromyalgia patients, who do not have a higher than usual energy demand and who experience constant pain in both muscular and non-muscular tissue.

This invention provides ribose for the alleviation of pain and fatigue and irritable bowel syndrome experienced by patients with fibromyalgia. The alleviation of pain and fatigue in turn is reflected in an increased feeling of well-being and energy. By "alleviation" is meant the definition as set forth in Webster's Ninth New Collegiate Dictionary: "alleviate . . . " to make (as suffering) more bearable." In this case, a noticeable reduction in the levels of pain, achiness, fatigue and a noticeable improvement in bowel function, as reported subjectively by the patient. A convenient composition comprised of ribose, magnesium, malic acid, vitamins C, $B_3$ and $B_6$, tryptophan, calcium, zinc and ornithine or arginine is also provided. Preferably, this composition is mixed in eight ounces of water and taken orally two to four times a day. This invention also provides doses and protocols for maximum beneficial effect.

Ribose is a simple 5-carbon sugar, with a slightly sweet taste. It is a white to light yellow crystalline powder. The amount necessary to alleviate symptoms of fibromyalgia can be between 2 and 50 grams per day depending on severity of the condition and the individual response to ribose ingestion. The preferred dose is around 20 grams per day taken in 10 gram doses twice a day or 5 gram doses 4 times per day. The ribose can be ingested directly, sprinkled on food, or mixed in a liquid such as water, juice, coffee, or tea. Ribose could also be ingested as part of an energy bar or other functional food. In the most serious cases, ribose could also be administered by other methods such as intravenous, intraperitoneal, or transmucosal delivery.

We have found that the steady ingestion of ribose two to four times per day over the course of a week is enough to observe noticeable improvement in the level of fatigue, achiness, pain, and energy, and alleviation of irritable bowel syndrome. Continued ingestion leads to greater improvement, in turn allowing the patient to endure the much needed regular exercise to further relieve the painful symptoms.

A convenient premixed composition containing the recommended dose of ribose plus other ingredients that address other symptoms of fibromyalgia may provide added benefit.

The following examples are included to demonstrate the preferred embodiment of the invention. D-ribose is the preferred embodiment, however, to those skilled in the art it is known that certain pentoses such as xylitol and ribulose are readily converted to D-Ribose in vivo. Therefore, the term "ribose" is intended to include D-Ribose and such precursors thereof. It should be appreciated by those skilled in the art that the methods and dosages in the examples that follow represent methods and dosages discovered by the inventors to function well in the practice of this invention, and thus can be considered to constitute preferred modes for its practice. However, those skilled in the art should, in light of the present disclosure, appreciate that many changes can be made in the specific embodiments that are disclosed and still obtain a like or similar result without departing from the concept and scope of the invention. All such changes are considered to be within the spirit, scope, and concept of the invention as defined by the appended claims.

EXAMPLE 1

Alleviation of Symptoms in a Fibromyalgia Patient

A female patient diagnosed with fibromyalgia had been experiencing extreme muscle pain and fatigue as well as irritable bowel syndrome, disturbed sleep, and cognitive dysfunction. She had been told by her physician that she was in the worst stage of the condition and could end up in a wheel chair within a year. She began taking ribose, one teaspoonful (about 5 grams), 4 times per day. She felt an immediate improvement in her symptoms and noticed that she had more energy and fewer flare ups of muscle soreness. She continued taking it for a week then decided to observe the effects of stopping the doses of ribose, so she discontinued the protocol for one week. The symptoms returned to their previous level. She resumed taking one teaspoonful 4 times per day and after 4 weeks reported that it not only alleviated her pain, fatigue and morning stiffness, but also improved her irritable painful bowel syndrome. She stated that "It is without a doubt the best product I have ever been on."

EXAMPLE 2

Pilot Study on the Effect of Ribose in Alleviating the Symptoms of Fibromyalgia

Four women subjects ranging in age from 45 to 55 were given ribose and instructed to take at least 20 grams per day, preferably divided in four doses. The recommended mode of administration was one heaping teaspoon, about five to seven grams, mixed in six to eight ounces of water, taken preferably with meals and before planned activity. Subjects were encouraged to vary the dosage according to their perceived needs. Each subject was given a health status profile (SF-36) to complete. The profile was to be filled out both before and after four weeks of ribose administration. Two of the subjects complied with filling out the profile.

Health Status Profile (SF-36):

1) General health compared to one year ago: 1=much better, 2=somewhat better, 3=about the same, 4=somewhat worse, 5=much worse
2) Energy, 2 questions, from peppy all of the time to none of the time.
3) Activities, 12 examples from vigorous to mild, scored as: limited a lot, limited a little, not limited
4) Pain: 1=none, 2=very mild, 3=mild, 4=moderate, 5=severe, 6 =very severe The results of each subject's before and after ratings are summarized in Table I.

TABLE I

| Subject, age | General health compared to last year before/after | Energy before/after | Activities (12 total) before/after | pain before/after |
|---|---|---|---|---|
| #1 45–54 Fibromyalgia for 15 years | much worse somewhat better | little of the time all of the time | 8 of 12 limited a lot 1 of 12 limited a lot | very severe moderate |
| #2 50–55 Fibromyalgia for several years | somewhat better much better | none of the time some of the time | 2 of 12 limited a lot 0 of 12 limited activities | severe moderate |

Each of these subjects reported a drop in energy and increase in aching within a day of suspending ribose administration.

Subject #3, age 52, who was compliant with the protocol but did not complete the profile, reported that she experienced an improvement in her fatigue level and less achiness. She began to feel more energetic, but did not feel a decrease in severe pain at the tender points. Cessation of administration resulted in next-day loss of energy.

Subject #4, age 50–55, who did not complete the profile, also did not follow the protocol. Nonetheless, she reported that when she felt exhausted, she would take ribose and feel more energetic.

As can be seen, no subject reported total relief from all symptoms of fibromyalgia, but all reported some alleviation.

EXAMPLE 3

Treatment of Fibromyalgia With Oral Ribose

Following the informal studies in five subjects, a protocol was written to determine whether oral ribose administration in patients with fibromyalgia (FM) can reduce symptoms of fatigue and pain and improve the subjects' quality of life. The study endpoints will be: (1) the patient's visual analog (PVA) scale for pain, (2) the patient's analog scale for fatigue, (3) the physician's global assessment ($GA_{phs}$), (4) the patient's global assessment ($GA_{PT}$), (5) the Western Ontario MacMaster Questionaire (WOMAC) index, (6) SF-36 quality of life form, (7) the patient's's daily activity/events log and (8) the number of days to study discontinuation, if the patient chooses to do so, based upon his/her improved condition.

The details of the WOMAC index and the PVA are as follows:

I.a. Patient Visual Analog (PVA) scale for assessment of pain at tender points (Vertical lines to be drawn by patient and quantitated by physician)

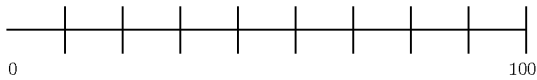

0                                                                 100

I.b. Patient Visual Analog (PVA) scale of assessment of fatigue

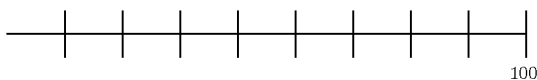

100

II. Physician's Global Assessment (GAPHYS)
   Patient's Global Assessment (GAPT)
   Scale: With respect to FM general condition)

☐ Very good   ☐ Good   ☐ Fair   ☐ Poor   ☐ Very poor

III. FM Assessment
   1. PAIN
      ☐ Pain at night
      ☐ Pain with Movement
      ☐ Pain without Movement 2. MORNING (A.M.) STIFFNESS
      ☐ No Pain
      ☐ Less than (<) 15 minutes
      ☐ Greater than (>) 15 minutes 3. WALKING DISTANCE
      ☐ More than 1 Mile
      ☐ ½ to 1.0 Miles
      ☐ ¼ to ½ Mile
      ☐ Less than ¼ Mile 4. PAIN WHILE WALKING
      ☐ No pain
      ☐ Pain early after starting to walk
      ☐ Pain only after walking some distance 5. WALKING UP FLIGHT OF STAIRS
      ☐ No difficulty
      ☐ Some difficulty
      ☐ Impossible 6. WALKING DOWN FLIGHT OF STAIRS
      ☐ No difficulty
      ☐ Some difficulty
      ☐ Impossible 7. STOPPING OR SQUATTING TO FLOOR
      ☐ No difficulty
      ☐ Some difficulty
      ☐ Impossible 8. WALKING UP/DOWN HILLS
      ☐ No difficulty
      ☐ Some difficulty
      ☐ Impossible Following is a study Event Schedule to be used for protocol compliance and patient monitoring during the clinical study.

SECTION C

INSTRUCTIONS:
The following questions concern your physical function. By this we mean your ability to move around and to look after yourself. For each of the following activities, please answer each question with an "X" in the appropriate box to indicate the degree of difficulty you have experienced during the last 48 hours due to pain or fatigue.

What degree of difficulty did you have with...

| QUESTION: | None | Mild | Moderate | Severe | Extreme |
|---|---|---|---|---|---|
| 1. Descending stairs. | ☐ | ☐ | ☐ | ☐ | ☐ |
| 2. Ascending stairs. | ☐ | ☐ | ☐ | ☐ | ☐ |
| 3. Rising from sitting. | ☐ | ☐ | ☐ | ☐ | ☐ |
| 4. Standing | ☐ | ☐ | ☐ | ☐ | ☐ |
| 5. Bending to floor. | ☐ | ☐ | ☐ | ☐ | ☐ |
| 6. Walking on flat surface. | ☐ | ☐ | ☐ | ☐ | ☐ |
| 7. Getting in/out of car. | ☐ | ☐ | ☐ | ☐ | ☐ |
| 8. Going shopping. | ☐ | ☐ | ☐ | ☐ | ☐ |
| 9. Putting on sock/stockings. | ☐ | ☐ | ☐ | ☐ | ☐ |
| 10. Rising from bed. | ☐ | ☐ | ☐ | ☐ | ☐ |
| 11. Taking off sock/stocking. | ☐ | ☐ | ☐ | ☐ | ☐ |
| 12. Lying in bed. | ☐ | ☐ | ☐ | ☐ | ☐ |
| 13. Getting in/out of bath. | ☐ | ☐ | ☐ | ☐ | ☐ |
| 14: Sitting. | ☐ | ☐ | ☐ | ☐ | ☐ |
| 15. Getting on/off toilet. | ☐ | ☐ | ☐ | ☐ | ☐ |
| 16. Heavy domestic duties. | ☐ | ☐ | ☐ | ☐ | ☐ |
| 17. Light domestic duties. | ☐ | ☐ | ☐ | ☐ | ☐ |

WOMAC INDEX
SECTION A

INSTRUCTIONS:
Answer each question with an "X" in the appropriate box, based on fatigue or the amount of pain you experienced in your muscles. For each situation, enter the amount of pain experienced doing the last 48 hours.

How much pain do you have?

| QUESTION: | None | Mild | Moderate | Severe | Extreme |
|---|---|---|---|---|---|
| 1. Walking on a flat surface. | ☐ | ☐ | ☐ | ☐ | ☐ |
| 2. Going up or down stairs. | ☐ | ☐ | ☐ | ☐ | ☐ |
| 3. At night while in bed. | ☐ | ☐ | ☐ | ☐ | ☐ |
| 4. Sitting or lying. | ☐ | ☐ | ☐ | ☐ | ☐ |
| 5. Standing upright. | ☐ | ☐ | ☐ | ☐ | ☐ |

SECTION B

INSTRUCTIONS:
Answer each question with an "X" in the appropriate box, based on the amount of muscle pain you experienced during the last 48 hours.

|  | None | Mild | Moderate | Severe | Extreme |
|---|---|---|---|---|---|
| 1. How severe is your pain after first awakening? | ☐ | ☐ | ☐ | ☐ | ☐ |
| 2. How severe is your pain after sitting, lying or resting later in the day? | ☐ | ☐ | ☐ | ☐ | ☐ |

The study will include 16 patients with a confirmed diagnosis of FM using a double-blind crossover design. All patients who meet entrance or screening criteria will be randomly assigned to either treatment #1 (oral dextrose as a placebo) or treatment #2 (oral ribose) at a dose of 20 gm per day (10 gm bid), as a first treatment modality. Both physician and patient will be blinded to the treatment modality. Informed consent will be obtained prior to enrolment. Patients will be administered either treatment, as randomly assigned. All endpoint parameters will be assessed at baseline prior to treatment, after 4 weeks of treatment one, at the end of the workout period, and again following 4 weeks of treatment 2 ("crossover" treatment modality). FIG. 1 is a summary of the protocol.

Patients will be included in the study if they present with a confirmed diagnosis of FM, as defined by the ACR criteria. All FM patients must have a PVA score of 40 or greater and have at least 11 of 18 tender points. Patients will be excluded from the study if (1) they do not meet ACR criteria for FM, (2) are diagnosed with rheumatoid or osteo-arthritis or gout, (3) suffer from coronary artery disease or recent myocardial infarction of less then three months, heart failure, diabetes mellitus, chronic obstructive/restrictive lung disease, hepatic or renal disease, cancer, or other metabolic disorders. In addition, all pregnant or lactating women will be excluded.

It is expected that, as in the pilot study, most of the patients will experience some alleviation of achiness, fatigue and/or pain at the tender points.

4. Convenient Composition for Administration of Ribose and Other Ingredients Although ribose is the primary ingredient for alleviating pain and fatigue, other compounds have been found beneficial in alleviating other symptoms of fibromyalgia. Magnesium, as magnesium carbonate, oxide, sulfate or citrate, has been found to enhance muscle energetics. Malic acid has shown some advantage in treating fibromyalgia. Calcium and zinc tend to relieve sleeplessness. Tryptophan, vitamins B3 and B6 are thought to be beneficial in the synthesis of serotonin, which affects mood. Omitine and/or arginine are precursors to growth hormone, low levels of which may be among the causes of fibromyalgia. Vitamins C is often borderline deficient in fibromyalgia patients and may be added to the composition. It is convenient for a patient to be able to administer these compounds in a single preparation. Table II shows a dry composition to be dissolved in eight ounces of water and administered twice daily.

TABLE II

|  | Preferred daily dosage | Acceptable daily range |
| --- | --- | --- |
| Ribose | 10 grams | 2 to 50 grams |
| Magnesium citrate | 500 mg | 200–1000 mg |
| Calcium carbonate | 500 mg | 200–1000 mg |
| Zinc citrate | 10 mg | 5–15 mg |
| Malic acid | 1300 mg | 800–1500 mg |
| Ornithine* | 2 mg | 1–10 mg |
| Vitamin C | 500 mg | 200–1500 mg |
| Vitamin $B_3$ | 10 mg | 5–30 mg |
| Vitamin $B_6$ | 120 mg | 50–200 mg |

*Arginine or citrulline may be substituted for ornithine.

The ingredients are triturated as a powder and can be conveniently administered in capsules, tablets or dissolved in any carrier, such as water or juice. If the solvent is water, many patients will prefer a sweeter composition with added flavor. The sweetener is most preferably sucrose. It is also convenient to prepare concentrated solutions which may be diluted to taste. It is most convenient to provide a drink with the composition of Table II dissolved in eight to ten ounces of water.

It will be understood by those skilled in the art that many subsitutions and additions may be made to the above invention without departing from the spirit and scope of the invention. Therefore, such substitutions and addtions are considered to be within the scope of the invention as herein claimed.

We claim:

1. A method to alleviate the symptoms of fibromyalgia syndrome comprising administering an effective amount of ribose to a patient suffering from fibromyalgia syndrome.

2. The method according to claim 1 wherein the amount of ribose is two to 60 grams per day.

3. The method according to claim 1 wherein the ribose is administered in at least two equal doses taken at least six hours apart.

4. A method to alleviate the symptoms of fibromyalgia syndrome in a patient suffering from fibromyalgia syndrome comprising administering a first effective amount of ribose in the morning and a second effective amount at least six hours after administration of the first effective amount.

5. The method according to claim 4 wherein the first amount of ribose is one to 30 grams and the second amount of ribose is one to thirty grams.

* * * * *